United States Patent
Patil et al.

(12)

(10) Patent No.: US 6,342,209 B1
(45) Date of Patent: Jan. 29, 2002

(54) COSMETIC COMPOSITIONS CONTAINING FILM FORMING POLYMERS PLASTICIZED WITH ESTERS AND MALIC ACID

(75) Inventors: Anjali Abhimanyu Patil, Westfield; Joseph Frank Calello, Bridgewater, both of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/564,448

(22) Filed: May 4, 2000

(51) Int. Cl.$^7$ .............................. A61K 7/00; A61K 7/04
(52) U.S. Cl. .......................................... 424/61; 424/401
(58) Field of Search .................................. 424/401, 400, 424/61, 63, 64, 70.1, 70.6, 70.7, 70.11, 70.12, 70.13, 70.14, 70.15, 70.16, 70.17

(56) References Cited

U.S. PATENT DOCUMENTS

| | | | | |
|---|---|---|---|---|
| 3,538,145 A | * | 11/1970 | Hirzy | 260/475 |
| 4,897,261 A | * | 1/1990 | Yamazaki et al. | 424/61 |
| 5,489,431 A | * | 2/1996 | Ascione et al. | 424/401 |
| 5,672,339 A | * | 9/1997 | Soyama et al. | 424/63 |
| 5,849,275 A | * | 12/1998 | Calello et al. | 424/64 |
| 5,908,631 A | * | 6/1999 | Arnaud et al. | 424/401 |
| 5,932,197 A | * | 8/1999 | Arnaud | 424/64 |
| 5,989,573 A | * | 11/1999 | Remy | 424/401 |
| 6,066,313 A | * | 5/2000 | Anton et al. | 424/63 |
| 6,110,447 A | * | 8/2000 | Ramin et al. | 424/61 |
| 6,190,677 B1 | * | 2/2001 | Remy | 424/401 |

* cited by examiner

*Primary Examiner*—Jose' G Dees
*Assistant Examiner*—Marina Lamm
(74) *Attorney, Agent, or Firm*—Julie Blackburn

(57) ABSTRACT

A cosmetic composition for application to keratinous surfaces containing at least one film forming polymer; and a plasticizer for the film forming polymer which is a $C_{1-20}$ ester of malic acid; and a method for plasticizing a film forming polymer contained in a cosmetic product which is applied to keratinous surfaces; comprising adding a plasticizing effective amount of a $C_{1-20}$ ester of malic acid to the cosmetic product composition.

20 Claims, No Drawings

COSMETIC COMPOSITIONS CONTAINING FILM FORMING POLYMERS PLASTICIZED WITH ESTERS AND MALIC ACID

TECHNICAL FIELD

The invention is in the field of cosmetic compositions for application to skin, nails or hair, which contain one or more film forming polymers.

BACKGROUND OF THE INVENTION

The application of cosmetic and personal care products to the skin almost always involves the formation of a film on the skin. For example, application of a foundation to the face involves formation of a colored film on the skin. The same is true of products such as lipstick, eyeshadow, blush, and nail enamel. The product is applied to the appropriate keratinous surface and allowed to dry. A film is formed which adheres to the skin for the appropriate period of time before being removed by chemical processes, or washed off with water.

Most film forming cosmetic and personal care products contain a polymeric material as the primary film former. The term "film former" means a material which, upon drying, produces a continuous film on keratinous substrates such as skin, hair, or nails. The term "skin" when used in accordance with the invention means both face and body skin or lips. The term "film forming polymer" means that the film former is in the polymeric form. A variety of polymers have film forming properties: they can be natural polymers, synthetic polymers, or polymers that have both natural and synthetic portions. While the polymers available today have a myriad of properties, most cosmetics and personal care products contain other ingredients to further modify the properties of the composition and improve aesthetics.

When forming a film on skin, hair, or nails, it is important that the film have certain properties in order to provide a commercially acceptable product. For example, if the film formed is too brittle, it may crack, or chip from the keratinous surface. On the other hand, if the film is not hard enough, it may be tacky to the touch and the consumer will have the feeling that the product has not dried on the skin. Accordingly, most cosmetic and personal care products containing one or more film forming polymers also contain an ingredient known as a plasticizer. A plasticizer is a material that is capable of modifying the properties of the film formed on the keratinous substrate by the film forming polymer. Generally, the plasticizer will make the film more flexible, or pliable. This, in turn, causes the film to "move with the skin" in products which are applied to skin. In products such as nail enamel, the plasticizer will make the film formed on the nail more flexible such that it doesn't chip from the nail so readily. Further, the plasticizing effect of the most desirable plasticizers does not dissipate with time, e.g. some plasticizers have only a temporary plasticizing effect, and after passage of time, lose effectiveness. A plasticizer is a most important ingredient in cosmetic and personal care products containing polymeric film formers. The selection of the appropriate plasticizer can mean the difference between a successful, aesthetically pleasing product, and a product that is unacceptable from the commercial point of view.

Accordingly, there is always a need for better plasticizers in film forming cosmetic and personal care products. An ideal plasticizer is capable of plasticizing a wide variety of film forming polymers, and enable the selection of a wide variety of film forming polymers for use in compositions. It has been discovered that certain esters of malic acid provide an excellent plasticizing effect to a wide variety of natural and synthetic polymeric film formers.

An object of the invention is to provide an improved plasticizer for use in film forming cosmetic and personal care products.

Another object of the invention is to provide cosmetic and personal care products containing one or more polymeric film formers, which contain $C_{1-20}$ esters of malic acid as a plasticizing agent for the film forming polymers.

Another object of the invention is provide cosmetic and personal care products containing one or more film forming polymers, where the plasticizer for the film forming polymer does not lose effectiveness over time.

Another object of the invention is to provide a method for plasticizing a film formed on skin, nails, or hair with a cosmetic composition containing one or more film forming polymers, comprising adding to said film a plasticizing effective amount of a $C_{1-20}$ ester of malic acid.

SUMMARY OF THE INVENTION

The invention comprises a cosmetic composition for application to keratinous surfaces containing at least one film forming polymer; and a plasticizer for the film forming polymer which is a $C_{1-20}$ ester of malic acid.

The invention also comprises a method for plasticizing a film forming polymer contained in a cosmetic product which is applied to keratinous surfaces, comprising adding a plasticizing effective amount of a $C_{1-20}$ ester of malic acid to the cosmetic product composition.

DETAILED DESCRIPTION

All percentages mentioned herein are percentages by weight unless otherwise indicated.

I. THE COSMETIC COMPOSITIONS

A. The Film Forming Polymer

A wide variety of film forming polymers may be used in the cosmetic or personal care products of the invention. The film forming polymer must be capable of forming a film on the skin, nails, or hair. The film forming polymers may be natural or synthetic, or a combination of both, and may be in the form of solids, semi-solids, or liquids. The film forming polymer may be neutral or ionic in character, e.g. anionic, cationic, nonionic, or amphoteric.

1. Synthetic Polymers

Suitable synthetic polymers include homopolymers, copolymers, and block and graft copolymers comprised of repeating monomers such as acrylic or methacrylic acid or esters thereof, urethanes, esters, amides, styrene, vinyl, silicon, and so on. The synthetic polymers may be present in the composition in ranges from 0.1–95%, preferably 1–85%, more preferably 3–45% by weight of the total composition.

Examples of synthetic film forming polymers include those set forth in the CTFA Cosmetic Ingredient Dictionary and Handbook, Eighth Edition, 2000, pages 1744 through 1747, which are hereby incorporated by reference, including those which are summarized herein.

a. Silicone Resins

Cross-linked silicones, also known as silicone resins, can be plasticized with $C_{1-20}$ esters of malic acid, and are suitable for use in the compositions and method of the invention. Preferred silicone resins have the general formula:

[(RR'R")₃SiO₁/₂]ₓ [SiO₂]ᵧ wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

b. Copolymers of Silicone and Organic Monomers

Also suitable for use as the film forming polymer in the compositions and method of the invention are copolymers of silicone and various organic, ethylenically unsaturated monomers, and optionally other monomers. Examples of such polymers are disclosed in U.S. Pat. No. 6,033,650, which is hereby incorporated by reference. Preferred examples of these polymers include graft or block copolymers comprised of silicon moieties and C1–12 alkyl acrylate or methacrylate monomers which may be substituted with one or more groups such as halogen or hydroxy, also referred to as silicone/acrylate copolymers. Suitable silicone acrylate copolymers may be purchased from 3M Company under the tradenames VS-70 and SA-70, or from Shin Etsu Silicones.

c. Urethane Homo- and Copolymers

Also suitable for use in the compositions and method of the invention are homo and copolymers of urethane. Homopolymers of urethane are often sold in an aqueous dispersion from vendors such as Alloid Colloids, B.F. Goodrich, and the like. Suitable urethane copolymers may be comprised of urethane monomers copolymerized with organic compounds, or other synthetic monomers.

d. Amides and Amines

Also suitable are various synthetic polymers containing amide or amine substituent groups. Examples of such polymers include nylon, ammonium polyacrylate, acrylamides copolymer, acrylates/acrylamide copolymers, acrylates ammonium acrylate copolymer, acrylates C10–20 alkyl acrylate cross polymer, acrylates/carbamate crosspolymer, acrylates ceteth-20 itaconate copolymer, acrylates/dimethylaminoethyl methacrylate copolymer, ammonium acrylates copolymer, ammonium polyacrylate, ammonium styrene/acrylates copolymer, ammonium vinyl acetate/acrylates copolymer, aminomethylpropanol/acrylates/dimethylaminoethylmethacrylate copolymer, and so on.

e. Other Synthetic Polymers

Preferred are synthetic polymers are comprised of one or more monomers selected from the following general formula:

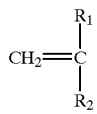

wherein $R_1$ is H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl which may be substituted with one or more halogens.

Even more preferred as synthetic polymers which comprise polar monomers such as acrylic acid or methacrylic acid, in combination with $C_{1-6}$ esters thereof Most preferred is a synthetic polymer which comprises monomers of butyl methacrylate and acrylic acid.

2. Natural Polymers

A variety of natural polymers, or derivatives thereof are suitable, including cellulosics, chitins, chitosans, shellac, rosins, resins, animal or vegetable proteins and polypeptides, and so on. The natural polymers may be present in ranges from 0.1–95%, preferably 1–85%, more preferably 3–45% by weight of the total composition.

a. Cellulosics

Examples of suitable cellulosic polymers include nitrocellulose, mono- or diesters of cellulose formed by the reaction of cellulose with various organic acids, for example straight or branched chain carboxylic acids having from one to twenty, preferably one to ten carbon atoms, which may be substitued with one or more hydroxyl groups, Examples of such cellulosics include cellulose acetate, cellulose acetate isobutyrate, cellulose acetate propionate, cellulose acetate propionate carboxylate. Also suitable are cellulose polymers prepared by reacting with groups such as hydroxyl, alkoxyalkyl, hydroxylalkyl where the alkoxyalkyl and alkyl groups have from about one to ten carbon atoms. Examples of such polymers are carboxylmethyl hydroxyethylcellulose, carboxymethylcellulose, ethyl cellulose, hydroxyethylcellulose, methyl ethylcellulose, hydroxypropylcellulose, hydroxylbutyl cellulose, hydroxybutyl methylcellulose, and so on.

b. Chitin or Chitosan

Chitins, or chitosan and derivatives thereof are also suitable natural film forming polymers for use in the compositions and method of the invention. Chitin is defined as a polysaccharide derived from the exoskeleton of marine invertebrates which contains chiefly N-acetyl-glucosamine residues. Chitosan is chitin that has been deacetylated. Both polymers may be used as is, or esterified to form mono-, di-, or triesters by reacting with various straight or branched chain organic acids having from one to thirty carbon atoms, alpha or beta hydroxy acids, or di- or tricarboxylic acids. Examples of chitin or chitosan esters include chitosan adipate, chitosan ascorbate, chitosan formate, chitosan glycolate, chitosan lactate, chitsan PCA, chitosan salicylate, chitosan succinamate, and so forth. Also suitable are simple derivatives of chitin or chitosan, which are formed by substituting moieties such as hydroxyl, $C_{1-6}$ alkoxy, and the like on the polymer. Examples of such derivatives include carboxylbutyl chitosan, carboxylmethyl chitosan, carboxyethyl chitosan, carboxylbutyl chitosan, and so on.

c. Proteins

Also suitable as film forming polymers are various animal and vegetable proteins including hydrolyzed animal protein, albumin, serum albumin, hydrolyzed wheat protein, hydrolyzed soy protein, hydrolyzed animal collagen, and mixtures thereof.

d. Dextrans

Also suitable are dextrans and alkoxy, or alkoxylalkyl derivatives thereof such as carboxymethyl dextran, carboxylethyl dextran, and so on.

e. Rosins, Resins and Gums

Also suitable are various natural resins and rosins and derivatives thereof such as Balsam Canada resin, hydrogenated rosin, glycol rosinate, shellac, and the like. Various gums are also suitable including acacia gum, and similar materials.

It may be desirable to have more than one film forming polymer in the composition. They polymers may be a combination of one or more synthetic polymers, or one or more natural polymers, or mixtures of both.

B. The Plasticizer

The The nail enamel compositions of the invention comprise a plasticizing effective amount of a $C_{1-20}$ mono- or diester of malic acid. The plasticizing effective amount may vary depending on the film forming polymer and solvents, as well as the other ingredients in the formula. Generally, suggested ranges of plasticizer range from 0.01 to 50%, preferably 0.1–40%, more preferably 0.2–35% by weight of the total composition. Preferred are diesters of malic acid, more particularly, fatty diesters of malic acid which are formed by the reaction of a C1–20 alcohol with malic acid. Preferably, the plasticizer is formed by the reaction of a C1–8 alcohol and malic acid, and is dioctyl malate or dibutyl malate.

C. Other Ingredients

A wide variety of other ingredients may be found in the cosmetic compositions, depending on the type of composition. For example, the compositions may include nail enamel, foundation makeup, blushes, lipsticks, skin creams and lotions, concealers, and hair products such as shampoos, conditioners, and sprays.

1. Nail Enamel Compositions

The cosmetic compositions may comprise nail enamel. Suitable nail enamel compositions contain, in addition to the film forming polymer and the plasticizer, one or more aqueous or non-aqueous solvents, secondary film formers, pigments, suspending agents, and the like.

a. Solvents

The nail enamel compositions of the invention comprise 10–95% by weight of the total composition, of solvent. The solvent may be aqueous or non-aqueous or a mixture of both types of solvents. Suitable non-aqueous solvents include aliphatic or aromatic ketones such as acetone, diacetone alcohol, dihydroxyacetone, ethyl butyl valerolactone, methyl ethyl ketone, and the like; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate,hexyl alcohol, isopropanol, and the like; glycol ethers; esters such as butyl acetate, ethyl acetate, etc.

b. Pigments

The nail enamel compositions of the invention may be pigmented or clear. If pigmented, generally 0.1–30% by weight of the total composition, preferably 0.5–20%, more preferably 1–15% of pigment is suggested. Pigments suitable for use in nail enamel compositions are well known and include iron oxides, D&C and FD&C colors, titanium dioxide, and the like. The pigments may be treated or coated with agents which modify the surface properties such as silicones. Examples of silicone treated pigments which can be used in the compositions of the invention are set forth in U.S. Pat. No. 4,832,944, which is hereby incorporated by reference.

c. Suspending Agents/Associative Thickeners

If the nail enamel compositions of the invention contain pigments, it is desirable to also incorporate 0.1–15% by weight of the total composition of a suspending agent which acts to suspend the pigments in the formulation. Suitable suspending agents are montmorillonite minerals and derivatives thereof, such as stearalkonium bentonite, hectorites, attapulgite, bentones, and the like, as well as polymeric compounds known as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl.

d. Silicones

It may also be desireable to include 0.1–20% by weight of the total composition, of a silicone antifoam agent in the nail enamel composition. Suitable silicone antifoam agents include dimethicone, or silicone glycol copolymers, which are polymethylsiloxanes wherein a portion of the methylsiloxane units are substituted with polyalkylene glycol ether moieities. Preferred is wherein about 60–90% of the polymer (the percentage being based on the number of monomer units), of the compound is polydimethylsiloxane or polyhydrogen methylsiloxane and 30–40% of the compound (the percentage being based upon the number of monomer units) is di- methyl or hydrogen-methyl siloxane units substituted with polyalkylene glycol ethers. Most preferred are silicone glycol copolymers having a viscosity ranging from 1.0 to 500,000, preferably 1.0 to 2,000 centipoise at 25° C., a specific gravity ranging from 0.80 to 1.030 at 25° C., and comprise approximately 80% dimethylsiloxane units and 20% propylene oxide substituted methyl siloxane units. Silicone glycol copolymers having this description are commercially available from a variety of sources including Dow Corning under the tradenames Dow Corning Additive 3, 7, 11, 14, 18, 21, 24, 26, 28, 29, 51, 54, 56, 57, and 1248.

The compositions of the invention may also contain other ingredients such as emulsifiers, humectants, ancillary film formers, defoamers, plasticizers, preservatives, and the like.

2. Foundation Makeup

Foundation makeup compositions are typically found in the emulsion form, either water-in-oil, or oil-in-water emulsions, and contain a film forming polymer, pigments, and one or more surfactants, which cause the composition to form a stable emulsion. Generally, these compositions comprise from about 0.5–95%, preferably 1–90%, more preferably 5–75% water, and 0.5–99%, preferably 1–90%, more preferably 2–40% oil. The film forming polymer may be part of the oil phase or part of the water phase, provided it is capable of forming a film on the skin and is capable of being plasticized by contact with the $C_{1-20}$ ester of malic acid.

a. Silicone or Organic Oils

The makeup compositions may contain one or more silicone oils. The silicone oil may be volatile, non-volatile or a mixture of both, provided that the silicone oils are soluble in each other, and in the oil phase of the composition. Suitable volatile silicones include Cyclic silicones (or cyclomethicones) are of the general formula:

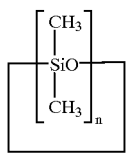

where n=3–7.

Linear volatile silicones in accordance with the invention have the general formula:

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Suitable nonvolatile silicones include water insoluble silicones having a viscosity of 10 to 600,000 centistokes, preferably 20 to 100,000 centistokes at 25° C. Suitable water insoluble silicones include cetyl dimethicone, dimethicone, phenyl trimethicone, phenyldimethicone, diphenyl dimethicone, and mixtures thereof Such silicones are available from Dow Corning as the 3225C formulation aid, Dow 190 and 193 fluids, or similar products marketed by Goldschmidt under the ABIL tradename.

Also suitable as the nonvolatile silicone oil are various fluorinated silicones such as trimethylsilyl endcapped fluorosilicone oil, polytrifluoropropylmethylsiloxanes, and similar silicones such as those disclosed in U.S. Pat. No. 5,118,496 which is hereby incorporated by reference.

A variety of organic oils may also be suitable. Examples of suitable organic oils include hydrocarbons, esters, and the like. Suitable hydrocarons include paraffinic hydrocarbons having 9 to 70 carbon atoms, C20–45 olefins, isododecane, isobutene, isoeicosane, isohexadecane, mineral oil, squalene, squalane, and the like.

Also suitable are various esters that are liquid at room temperature. Suitable esters include guerbet esters, which are generally defined as esters which are formed by the reaction of a guerbet alcohol (which is a branched chain alcohol) with a mono-, di-, or tricarboxylic acid.

Other suitable esters include those having the formula RCO—OR' wherein R and R' are each independently a $C_{1-25}$, preferably a $C_{4-20}$, straight or branched chain alkyl, alkenyl or alkoxycarbonylalkyl or alkylcarbonyloxyalkyl. Preferred are esters which are the reaction product of of a branched chain fatty acid and a branched or straight chain fatty alcohol, preferably a branched chain fatty alcohol. Examples of such esters include isotridecyl isononanoate, isostearyl neopentanoate, tridecyl neopentanoate, cetyl octanoate, cetyl ricinoleate, decyl isostearate, isodecyl oleate, isodecyl neopentanoate, isohexyl neopentanoate, tridecyl octanoate, and so on.

Other suitable esters include naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl linoleate, glyceryl myristate, glyceryl isostearate, PEG castor oils, PEG glyceryl oleates, PEG glyceryl stearates, PEG glyceryl tallowates, and so on.

b. Pigments or Powders

Suitable colorants may be inorganic or organic pigments and powders. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments also generally consist of insoluble metallic salts of certified color additives, referred to as the Lakes. Inorganic pigments include iron oxides, ultramarines, chromium, chromium hydroxide colors, and mixtures thereof Preferably, the pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Particularly preferred are silicone treated pigments as disclosed in U.S. Pat. No. 5,143,722, which is hereby incorporated by reference. Suggested ranges of pigments found in foundations is about 0.1–30%, preferably 0.5–25%, more preferably 1–20% by weight of the total composition.

Preferably, the composition contains one or more particulates which serve as powders, fillers, or sunscreens in the composition. These powders or fillers are present for adjusting the color of the composition, and in some cases may provide a sunscreen effect by physical blocking of UV radiation. Preferably, the particle size of the particulates ranges from 0.05 to 100 microns, and are present in ranges of 0.1–20%, preferably 0.5–15%, more preferably 1–10% by weight of the total composition. Examples of particulates include white or non-pigmentitious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. While titanium dioxide is commonly considered to be a white pigment when used in paints, in color cosmetic compositions it is used more for its ability to mute color, and/or provide an opaque or semi-opaque finish, or provide sunscreen protection, then as a colorizing ingredient. The above mentioned particulates may be surface treated with lecithin, amino acids, mineral oil, silicone oil or various other agents either alone or in combination, which coat the powder surface and render the particles more lipophilic in nature.

c. Surfactants

The foundation makeup compositions generally will contain one or more surfactants which are capable of ensuring stability of the emulsion formed. Suitable surfactants may be organic or silicone surfactants. The compositions of the invention comprise an effective amount of a surfactant which is capable of causing the water phase and the oil phase to form an emulsion having stability for two weeks at 50° C. Suggested ranges of surfactant are in the range of about 0.1–20%, preferably 0.5–15%, more preferably 1–10% by weight of the total composition of one or more surfactants. Suitable surfactants include organic or silicone surfactants, which may be anionic, cationic, nonionic, zwitterionic, or amphoteric. Preferably the surfactants are nonionic organic or silicone surfactants.

Examples of nonionic organic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, laureth, 1–100 where the number of repeating ethylene oxide units is 1 to 100, and so on. Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol.

Also suitable as the nonionic surfactant are alkyoxylated carboxylic acids, which are formed by the reaction of a carboxylic acid with an alkylene oxide or with a polymeric ether. The resulting products have the general formula:

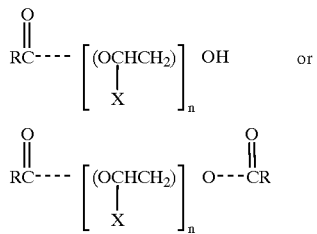

where RCO is the carboxylic ester radical, X is hydrogen or lower alkyl, and n is the number of polymerized alkoxy groups. In the case of the diesters, the two RCO- groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

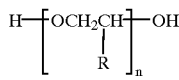

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

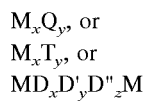

where $M_w$ is the molecular weight of the hydrophilic group portion and $M_o$ is the molecular weight of the lipophilic group portion.

The polymeric organosiloxane surfactant used in the invention may have any of the following general formulas:

$M_xQ_y$, or $M_xT_y$, or $MD_xD'_yD''_zM$ wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical. Preferred is a linear silicone of the formula:

$MD_xD'_yD''_zM$ wherein $M=RRRSiO_{1/2}$

D and $D'=RR'SiO_{2/2}$ $D'=RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy

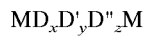

$D=Si[(CH_3)][(CH_2)_nCH_3]O_{2/2}$ where n=0–40,

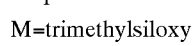

$D'=Si[(CH_3)][(CH_2)_o—O—PE)]O_{2/2}$ where PE is $(—C_2H_4O)_a(—C_3H_6O)_bH$, o=0–40, a=1–100 and b=1–100, and

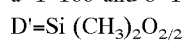

$D'=Si(CH_3)_2O_{2/2}$

More specifically, suitable silicone surfactants have the formula:

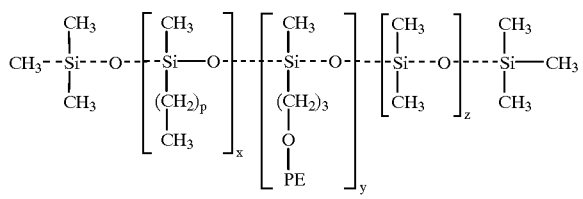

wherein p is 0–40, and

PE is (—C$_2$H$_4$O)$_a$(—C$_3$H$_6$O)$_b$—H where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark, which are referred to by the CTFA term "dimethicone copolyol."

Also suitable as nonionic silicone surfactants are hydroxy-substituted silicones such as dimethiconol, which is defined as a dimethyl silicone substituted with terminal hydroxy groups.

Examples of silicone surfactants are those sold by Dow Corning under the tradename Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

The foundation makeup compositions may contain a variety of other ingredients such as humectants, plant extracts, ceramides, emulsifiers, and the like.

3. Pigmented Cosmetic Sticks

The cosmetic compositions of the invention may be in the form of pigments sticks such as lipstick, eyeshadow sticks, foundation sticks, and the like. Preferably, these sticks are anhydrous, although they may, if desired, contain water. In addition to containing one or more of the film forming polymers and plasticizer in the ranges mentioned above, the compositions generally will also comprise a mixture of waxes and oils in amounts necessary to cause the formation of a stick. By "stick" is meant that the cosmetic composition is capable of forming a free standing stick. Also included within the meaning of the term "stick" are compositions that are capable of forming free standing sticks, but are poured into pans or similar types of containers.

a. Oils

The cosmetic stick generally comprises one or more oils. By "oil" is meant an oily material that is a liquid or semi-solid at room temperature. Preferably, the compositions contain 0.5–60%, preferably 1–50%, more preferably 2–45% by weight of the total composition. Suitable oils may vary widely and, in general, those oils listed as being acceptable in foundation makeup compositions in Section IC2(a) above, are also suitable for use in lipsticks.

b. Solidyfing Agent

Generally, a certain amount of a solidifying agent is necessary to enable the formation of a cosmetic stick. Most often solidyfing agents are waxes. The waxes are solid or semi-solid at room temperature. Suggested ranges of wax are 0.1–60%, preferably 0.5–55%, more preferably 1–45% by weight of the total composition. The waxes preferably have a melting point of about 39 to 135° C., preferably in the range of 45 to 95° C., most preferably 55 to 95° C. Suitable waxes generally include animal waxes, plant waxes, mineral waxes, silicone waxes, synthetic waxes, and petroleum waxes. More specifically, these waxes include tribehenin, bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, cetyl alcohol, beeswax, PEG-20 sorbitan beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like, as well synthetic homo- and copolymer waxes such as PVP/eicosene copolymer, PVP/hexadecene copolymer, and the like.

c. Pigments/Powders

Generally, cosmetic sticks will comprise 0.1–45%, preferably about 0.5–40%, more preferably 1–35% by weight of the total composition of pigments and/or powders. Suitable pigments and powders are as set forth above in Section IC2b.

The cosmetic stick compositions may also contain other ingredients to enhance the aesthetic properties, such as humectants, plant extracts, emulsifiers, and the like.

5. Mascara

The cosmetic compositions of the invention may be in the form of mascara. Generally mascaras are in the anhydrous or water and oil emulsion form. Anhydrous mascaras according to the invention generally comprise 0.1–95% oil, 0.5–30% pigment, 0. 5–45% of a solidifying agent, and 0.1–30% of one or more synthetic or natural film forming polymers, and 0.01–50% of the C$_{1-20}$ ester of malic acid plasticizer. The oils, pigments, and film forming polymers are those mentioned for use with the other cosmetics mentioned herein. Suitable solidifying agents are as mentioned herein with respect to the cosmetic sticks.

The mascara may also be in the form of an emulsion, which may be water-in-oil or oil-in-water. Typically such mascaras contain 0.1–50% water, 0.5–55% oil, 0.1–30% pigment, and 0.5–45% solidifying agent, and 0.1–30% of one or more synthetic or natural film forming polymers, and 0.01–50% of the C$_{1-20}$ ester of malic acid. Mascaras may also contain other desired ingredients such as humectants, preservatives, stabilizers, and so on.

The combination of the film forming polymer and C1–20 ester of malic acid may be used in a wide variety of cosmetic compositions. The C1–20 ester of malic acid acts as an excellent plasticizing agent for the film forming polymer, either alone, or when the combination is used in a cosmetic formula.

The invention will be further described in connection with the following examples which are set forth for the purposes of illustration only.

EXAMPLE 1

Nail enamel compositions in accordance with the invention were made as follows:

|  | w/w % | | | | |
|---|---|---|---|---|---|
|  | 1 | 2 | 3 | 4 | 5 |
| Dioctyl malate | 7.0 | 7.0 | 2.5 | 19.6 | 0 |
| Isopropyl alcohol | 9.0 | 9.0 | 12.8 | 8.4 | 10.5 |
| Polymer 1 | 9.0 | 9.0 | 20.6 | 52.3 | 65.0 |
| Polymer 2 | — | 75 | — | — | — |

-continued

| | w/w % | | | | |
|---|---|---|---|---|---|
| | 1 | 2 | 3 | 4 | 5 |
| Polymer 3 | — | — | 64.1 | — | — |
| Polymer 4 | — | — | — | 19.7 | 24.5 |

Polymer 1: a solution of 30% by weight of a terpolymer comprised of 70 parts methyl methacrylate, 20 parts butyl methacrylate, and 10 parts acrylic acid and 70% by weight of a mixture of 80 parts ethyl acetate and 20 parts butyl acetate.

Polymer 2: a solution of 30% by weight of a copolymer comprised of 60 parts methyl methacrylate, 20 parts butyl methacrylate, 20 parts ethyl hexyl methacrylate, and 10 parts acrylic acid, and 70% by weight of a mixture of 80 parts ethyl acetate and 20 parts butyl acetate.

Polymer 3: a solution of 41.4% by weight of a copolymer comprised of 90 parts of butyl methacrylate and 10 parts of acrylic acid, and 59.6% by weigh of a mixture of 80 parts ethyl acetate and 20 parts butyl acetate.

Polymer 4: a solution of 24.5% by weight of ½' nitrocellulose and 75.5% by weight of a mixture of 80 parts ethyl acetate and 20 parts butyl acetate.

The nail enamel compositions were prepared by combining all of the ingredients and mixing well.

EXAMPLE 2

The nail enamel compositions made in Example 1 were applied to glass plates evaluated for hardness on a scale of 1 to 10 with 1 being soft and 10 being hard. Hardness is an indication of how brittle, and prone to cracking, the film is. Films which are too brittle are considered to be not adequately plasticized. The most desirable hardness is about 2 to 5. The following results were obtained:

| Formula | 1 | 2 | 3 | 4 | 5 |
|---|---|---|---|---|---|
| Hardness Index | 4 | 4 | 4 | 3 | 8 |

The above results illustrate that nail enamel compositions containing no dioctyl malate exhibit a hardness index which is substantially greater than the hardness index of nail enamel compositions containing dioctyl malate.

EXAMPLE 3

A mascara composition in accordance wit the invention was made according to the following formula:

| | w/w % |
|---|---|
| 1 Water | QS |
| 2 Acacia gum | 1.97 |
| 4 Butylene glycol | 2.94 |
| 3 Methyl paraben | 1.96 |
| 3 Triethanolamine | 1.96 |
| 3 Black iron oxide | 10.78 |
| 3 Trisodium EDTA | 0.05 |
| 3 Silk Powder | 0.05 |
| 3 Hydrolyzed keratin | 0.05 |
| 4 Oleth-3-phosphate | 0.50 |

-continued

| | w/w % |
|---|---|
| 5 Rice wax | 1.96 |
| 5 Ditrimethylolpropane tetrastearate | 4.90 |
| 5 Polyethylene | 7.84 |
| 5 Ditrioctyldodecyl citrate | 0.50 |
| 5 Oleth-3 | 1.76 |
| 6 Stearic acid | 4.22 |
| 6 Dibutyl lauroyl glutamide | 1.37 |
| 7 Propyl paraben | 0.10 |
| 8 Phenoxyethanol | 0.98 |
| 9 Acrylic copolymer emulsion* (film forming polymer) | 11.77 |
| 10 Polyurethane-1** (film forming polymer) | 4.90 |
| 11 Dioctyl malate (plasticizer) | 0.10 |
| 12 PVP/hydrolyzed wheat protein | 0.10 |

*Flexbond ® 381 Emulsion Polymer - formaldehyde free vinyl acrylic copolymer, Air Products and Chemicals, Inc.
**Luviset ® P.U.R., Polyurethane 1, BASF.

Sequences 1 and 2 were pre-mixed at room temperature until the acacia gum was dispersed in water. Sequences 1 through 4 were ground in a colloid mill until the pigments were dispersed in the mixture (approximately 10 minutes). Sequences 5 and 6 were heated on a hot plate with continuous stirring at a temperature of approximately 110° C. until the mixture became clear, light yellow. The mixture was allowed to cool to 85 to 90° C., and Sequence 7 was then added with mixing. When the mixture was cooled to 40 to 45° C. Sequence 8 was added. The mixture was heated to 50° C. and Sequence 9 added. When the temperature of the mixture reach 60° C. Sequences 10, 11, and 12 were added. The mixture was cooled to room temperature and filled into mascara containers.

EXAMPLE 4

A makeup composition was made according to the following formula:

| | w/w % |
|---|---|
| Cyclomethicone | 3.00 |
| Propyl paraben/laureth-7 | 0.75 |
| Mica/methicone | 0.01 |
| Red iron oxide/methicone | 2.70 |
| Yellow iron oxide/methicone | 2.70 |
| Black iron oxide/methicone | 2.70 |
| Titanium dioxide/cyclomethicone/dimethicone copolyol | 14.10 |
| Zinc oxide/cyclomethicone/dimethicone copolyol | 5.00 |
| Cyclomethicone/Titanium dioxide/dimethicone copolyol/triethoxy caprylyl silane | 3.80 |
| Spherical silica | 0.15 |
| Nylon-12 | 1.00 |
| Boron nitride | 1.05 |
| Titanium dioxide/methicone | 1.00 |
| Dimethicone | 7.25 |
| Cyclomethicone | 5.80 |
| Tribehenin | 0.10 |
| Dioctyl malate | 0.03 |
| Dimethicone | 1.50 |
| Polyglyceryl-4-isostearate | 1.50 |
| Cyclomethicone/dimethicone | 3.40 |
| Water | 31.05 |
| Salicylic acid/hydrolyzed vegetable protein | 0.50 |
| Methoxypropylgluconamide | 0.50 |
| Magnesium ascorbyl phosphate | 0.01 |
| Ethyl paraben/propylene glycol | 5.75 |
| Propylene glycol | 2.37 |
| Tetrasodium EDTA | 0.01 |

-continued

|  | w/w % |
|---|---|
| Magnesium sulfate | 0.01 |
| Chamomile extract | 0.01 |
| Phytoclar | 0.01 |
| Silicone acrylate copolymer (film forming polymer) | 3.00 |
| Cyclomethicone/dimethiconol | 2.00 |
| Methyl dihydrojasmonate | 0.25 |

The composition was prepared by combining the ingredients and mixing well to form an emulsion. The resulting makeup composition was poured into containers.

EXAMPLE 5

A makeup composition was made as follows:

|  | w/w % |
|---|---|
| 1 Cyclomethicone/dimethicone copolyol | 20.85 |
| 1 Sorbitan sesquioleate | 0.05 |
| 1 Propyl paraben | 0.10 |
| 1 Titanium dioxide/methicone | 8.00 |
| 1 Red iron oxide/methicone | 0.47 |
| 1 Yellow iron oxide/methicone | 1.16 |
| 1 Black iron oxide/methicone | 0.18 |
| 1 Mica/dimethicone | 0.98 |
| 2 Nylon 12/lecithin | 2.00 |
| 2 Boron nitride | 3.90 |
| 2 Dioctyl malate (plasticizer) | 0.10 |
| 3 Cyclomethicone | 1.00 |
| 3 Dimethicone | 1.50 |
| 3 Dow Corning 2-0747 (film forming polymer) | 15.00 |
| 3 Tribehenin | 2.00 |
| 4 Glyceryl rosinate/C9-11 isoparaffin | 5.00 |
| 5 Water | 30.00 |
| 6 Methyl paraben | 0.20 |
| 6 Trisodium EDTA | 0.20 |
| 6 Butylene glycol | 4.50 |
| 7 SD alcohol 40-B | 3.00 |

The sequence 1 ingredients were milled in the colloid mill, one after the other until no undispersed white or color was present. Then sequence 2 ingredients were milled in until dispersed. In the main beaker, sequence 1 and 2 were charged and heated to 55–60° C. Then sequence 3 ingredients were added. When tribehenin was all melted, the sequence 4 ingredients were added. For the water phase, in a side beaker the sequence 5 ingredients and the pre-mix of sequence 6 were heated to 50–55° C. Right before emulsification, the sequence 7 ingredients were added to the water phase. The water phase and the oil phase were then emulsified using a homogenizer for 15 minutes. The mixture was cooled using a paddle mixer.

EXAMPLE 6

A mascara composition was made as follows:

|  | w/w % |
|---|---|
| Carnauba wax | 4.25 |
| Candelilla wax | 9.25 |
| Beeswax | 4.60 |
| Synthetic wax | 4.85 |
| BHA | 0.05 |
| Propyl paraben | 0.10 |

-continued

|  | w/w % |
|---|---|
| Glyceryl rosinate/$C_{9-11}$ isoparaffin | 12.00 |
| Lanolin acid | 6.00 |
| Isododecane | 16.40 |
| Dioctyl malate (plasticizer) | 1.00 |
| Black iron oxide | 10.00 |
| Silica | 4.50 |
| Polyethylene | 2.00 |
| Water | 7.60 |
| Methyl paraben | 0.35 |
| Sodium EDTA | 0.10 |
| Sodium dehydroacetate | 0.30 |
| Yeast glycoprotein | 1.00 |
| Hydrolyzed keratin (film forming polymer) | 0.05 |
| Ammonium hydroxide | 0.60 |
| Dow Corning 749 Fluid* (film forming polymer) | 15.00 |

*a mixture of 50 parts cyclomethicone and 50 parts trimethylsiloxysilicate.

EXAMPLE 7

A blush on was made as follows:

|  | w/w % |
|---|---|
| Dow Corning 749 Fluid (film forming polymer) | 32.50 |
| Dow Corning silastic Q7-4350 (silica, methyl and methyl vinyl siloxane copolymer) (film forming polymer) | 5.50 |
| Dimethicone/dimethiconol | 3.00 |
| Boron nitride | 4.90 |
| Dioctyl malate (plasticizer) | 0.10 |
| Talc | 4.00 |
| Water | 2.00 |
| Ethyl alcohol | 3.00 |
| Iron oxides | 3.00 |
| Red #30 lake | 1.80 |
| Titanium dioxide | 4.00 |
| Quaternium 18 hectorite/cyclomethicone | 20.00 |
| Cyclomethicone | 12.20 |
| Trifluoropropylmethylpolysiloxane | 4.00 |

EXAMPLE 8

A concealer was made as follows:

|  | w/w % |
|---|---|
| Dow Corning 749 fluid (film forming polymer) | 20.00 |
| Iron oxides | 4.00 |
| Titanium dioxide | 14.00 |
| Talc | 8.00 |
| Water | 3.00 |
| Ethyl alcohol | 3.00 |
| Dow Corning Silastic Q7-4350 (film forming polymer) | 7.00 |
| Dimethyl polysiloxane | 9.50 |
| Dioctyl malate (plasticizer) | 0.50 |
| Cyclomethicone | 19.00 |
| Trifluoropropylmethyl polysiloxane | 4.00 |

EXAMPLE 9

An eyeshadow formulation was made as follows:

|  | w/w % |
|---|---|
| Talc | 22.41 |
| Mica | 20.00 |
| Zinc stearate | 1.50 |
| Polyethylene/talc | 5.00 |
| Mica/titanium dioxide | 10.00 |
| Polyethylene | 1.50 |
| Bismuth oxychloride | 4.49 |
| Titanium dioxide | 4.00 |
| Black iron oxide | 0.15 |
| Yellow iron oxide | 0.35 |
| Red iron oxide | 0.60 |
| Dow Corning 749 fluid (film forming polymer) | 22.00 |
| Cyclomethicone | 2.00 |
| Cyclomethicone/dimethiconol | 2.50 |
| Dioctyl malate (plasticizer) | 0.50 |
| Coco caprylate caprate | 3.00 |

EXAMPLE 10

A sun-blocking cream was made as follows:

|  | w/w % |
|---|---|
| Dow Corning 749 Fluid (film forming polymer) | 30.00 |
| Iron oxides | 3.50 |
| Titanium dioxide | 20.00 |
| Zinc oxide | 5.00 |
| Boron nitride | 7.80 |
| Dioctyl malate (plasticizer) | 0.20 |
| Dow Corning Silastic Q7-4350 (film forming polymer) | 7.00 |
| Hexamethyl disiloxane | 10.00 |
| Cyclomethicone | 11.50 |
| Trifluoropropylmethyl polysiloxane | 5.00 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A nail enamel composition containing at least one film forming polymer; at least one solvent; and a plasticizer for the film forming polymer which is a $C_{1-8}$ ester of malic acid.

2. The composition of claim 1 wherein the film forming polymer is a selected from the group consisting of synthetic polymer, natural polymer, and mixtures thereof.

3. The composition of claim 2 wherein the synthetic film forming polymer is a synthetic polymer comprised of monomers selected from the group consisting of acrylic acid, acrylic acid esters, methacrylic acid esters, and mixtures thereof.

4. The composition of claim 3 wherein the acrylic acid esters are formed by the esterification of acrylic acid with a $C_{1-20}$ alcohol which is unsubstituted or substituted with one or more hydroxyl groups.

5. The composition of claim 3 wherein the methacrylic acid esters are formed by the esterification of methacrylic acid with a $C_{1-20}$ alcohol which is unsubstituted or substituted with one or more hydroxyl groups.

6. The composition of claim 2 wherein the film forming polymer is a natural polymer selected from the group consisting of cellulose, cellulose ester, and mixtures thereof.

7. The composition of claim 6 wherein the film forming polymer comprises nitrocellulose.

8. The composition of claim 1 which is a nail enamel containing a volatile organic solvent.

9. The composition of claim 8 which comprises:

0.1–95% of a film forming polymer, 0.1–40% of a plasticizer that is a $C_{1-8}$ ester of malic acid, 10–95% volatile organic solvent.

10. The composition of claim 9 further comprising 0.1–30% by weight of the total composition of pigment.

11. The composition of claim 10 further comprising 0.1–15% by weight of the total composition of suspending agent.

12. The composition of claim 10 further comprising 0.1–20% by weight of the total composition of a silicone anti-foam agent.

13. The composition of claim 1 wherein the ester of malic acid is a diester.

14. The composition of claim 13 wherein the ester of malic acid is dibutyl malate.

15. The composition of claim 13 wherein the ester of malic acid is dioctylmalate.

16. A method for plasticizing a film forming polymer contained in a nail enamel composition containing at least one film forming polymer and at least one organic solvent; comprising adding a plasticizing effective amount of a $C_{1-8}$ ester of malic acid to the nail enamel composition.

17. The method of claim 16 wherein the plasticizing effective amount is 0.01–50% by weight of the total cosmetic composition.

18. The method of claim 17 wherein the ester of malic acid is a diester of malic acid and is selected from the group consisting of dioctyl malate, dibutyl malate, or mixtures thereof.

19. The method of claim 18 wherein the nail enamel composition is pigmented.

20. The method of claim 18 wherein the film forming polymer is a synthetic polymer.

* * * * *